(12) United States Patent
Mikkaichi et al.

(10) Patent No.: US 8,784,304 B2
(45) Date of Patent: Jul. 22, 2014

(54) OVER-TUBE, METHOD OF MANUFACTURING OVER-TUBE, METHOD OF DISPOSING OVER-TUBE, AND METHOD OF TREATMENT IN ABDOMINAL CAVITY

(75) Inventors: Takayasu Mikkaichi, Tokyo (JP); Keita Suzuki, Tokyo (JP)

(73) Assignee: Olympus Corporation, Tokyo (JP)

( * ) Notice: Subject to any disclaimer, the term of this patent is extended or adjusted under 35 U.S.C. 154(b) by 1124 days.

(21) Appl. No.: 12/128,282

(22) Filed: May 28, 2008

(65) Prior Publication Data

US 2008/0228029 A1 Sep. 18, 2008

Related U.S. Application Data

(60) Division of application No. 10/962,000, filed on Oct. 8, 2004, now Pat. No. 7,645,230, which is a continuation of application No. PCT/JP2004/001363, filed on Feb. 10, 2004.

(60) Provisional application No. 60/446,447, filed on Feb. 11, 2003.

(51) Int. Cl.
 *A61B 1/04* (2006.01)

(52) U.S. Cl.
 USPC ........... 600/121; 600/104; 600/123; 600/124; 600/125

(58) Field of Classification Search
 USPC .......................... 600/121–125, 153–154, 159
 See application file for complete search history.

(56) References Cited

U.S. PATENT DOCUMENTS

| 5,297,536 | A | | 3/1994 | Wilk | |
| 5,386,817 | A | * | 2/1995 | Jones | 600/104 |
| 5,458,131 | A | | 10/1995 | Wilk | |
| 5,634,937 | A | | 6/1997 | Mollenauer et al. | |
| 6,485,467 | B1 | | 11/2002 | Crook et al. | |
| 7,721,742 | B2 | * | 5/2010 | Kalloo et al. | 600/115 |
| 2001/0049497 | A1 | * | 12/2001 | Kalloo et al. | 604/164.01 |

FOREIGN PATENT DOCUMENTS

| DE | 101 04 106 A1 | 8/2002 |
| EP | 0 807 416 A2 | 11/1997 |
| JP | 7-178108 | 7/1995 |

* cited by examiner

*Primary Examiner* — Matthew J Kasztejna
(74) *Attorney, Agent, or Firm* — Scully, Scott, Murphy & Presser, P.C.

(57) ABSTRACT

An over-tube for use in an endoscopic treatment in an abdominal cavity using an endoscope includes an over-tube main body which is inserted from a distal portion thereof via a natural opening in a patient's body to access the inside of the abdominal cavity from the distal portion through a lumen wall, and an internal cover which is disposed in a passage of the endoscope disposed in an inner cavity of the over-tube main body and which is extractable from a proximal portion of the over-tube main body.

7 Claims, 15 Drawing Sheets

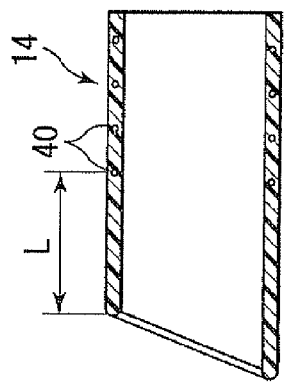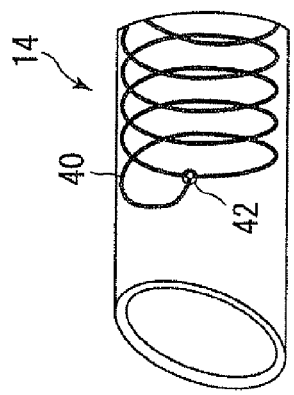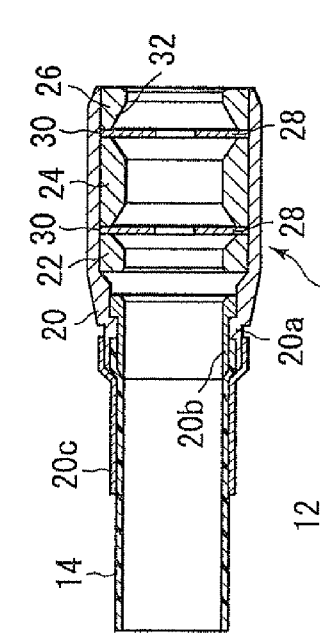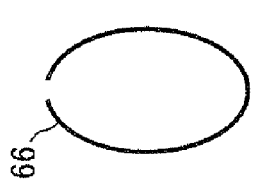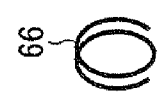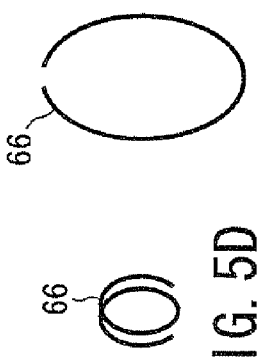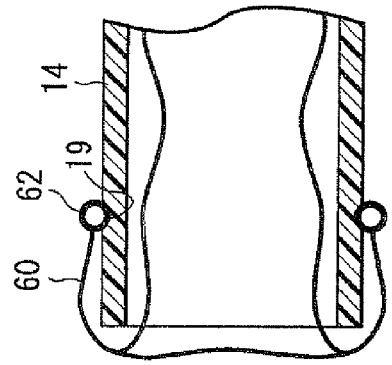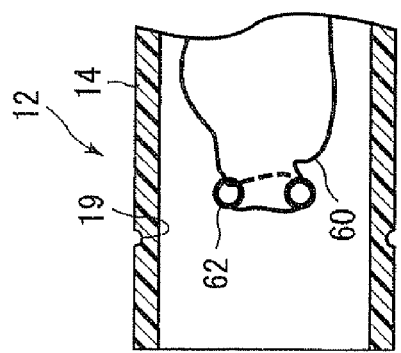

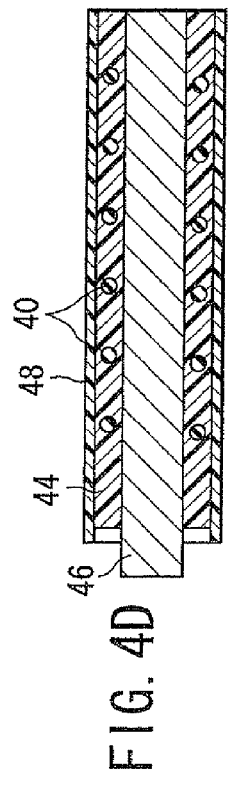
FIG. 4A
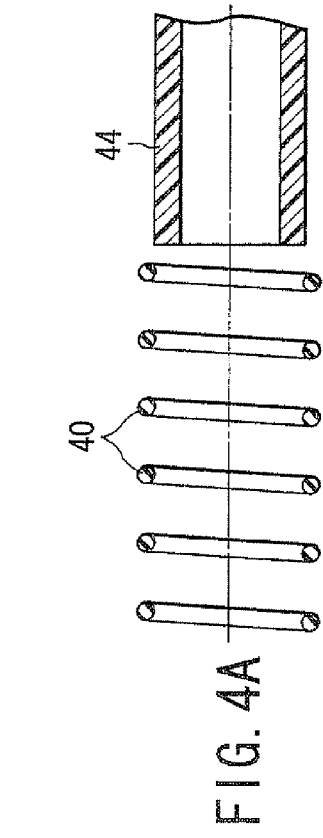
FIG. 4B
FIG. 4C
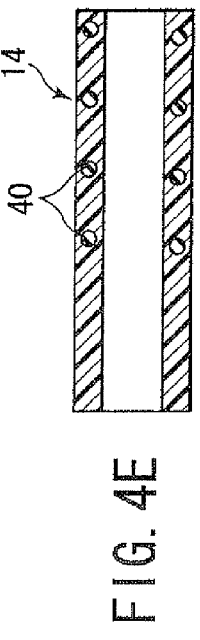
FIG. 4D
FIG. 4E
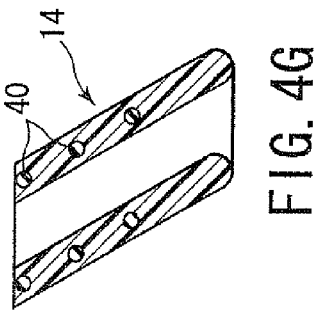
FIG. 4G
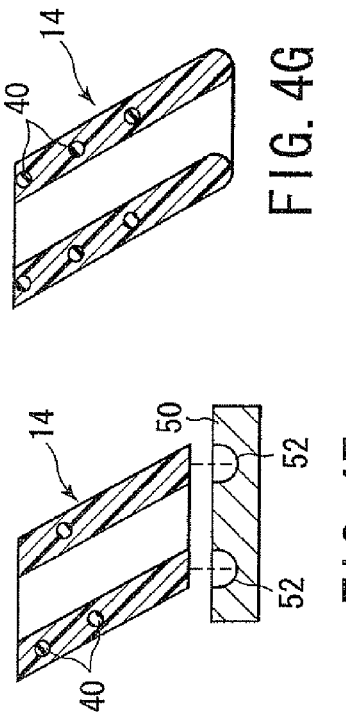
FIG. 4F

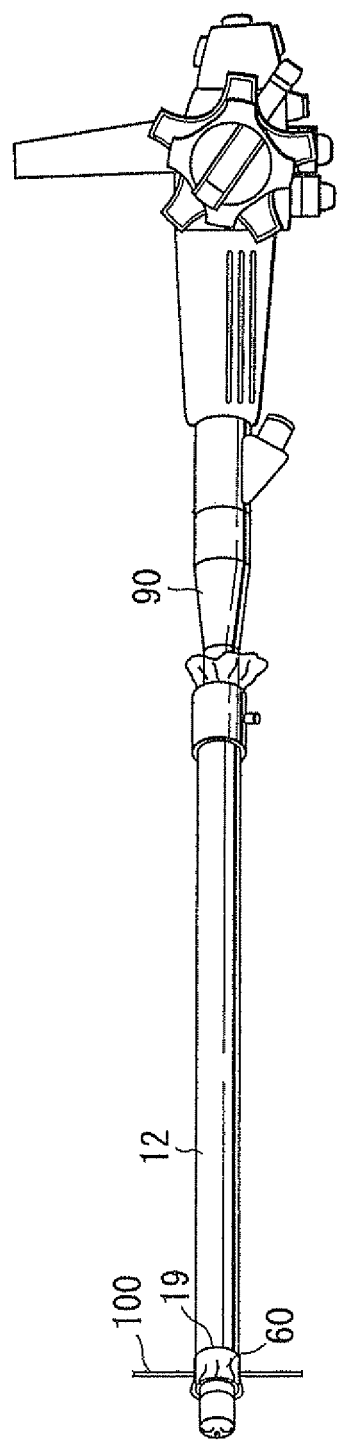
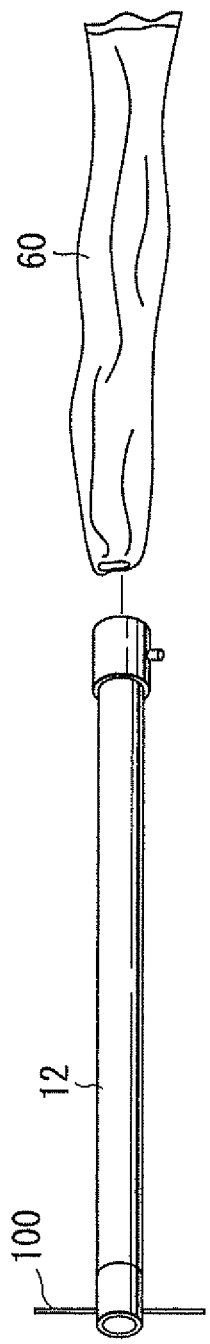
FIG. 7
FIG. 8

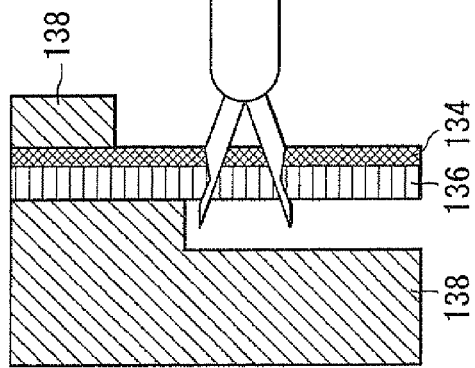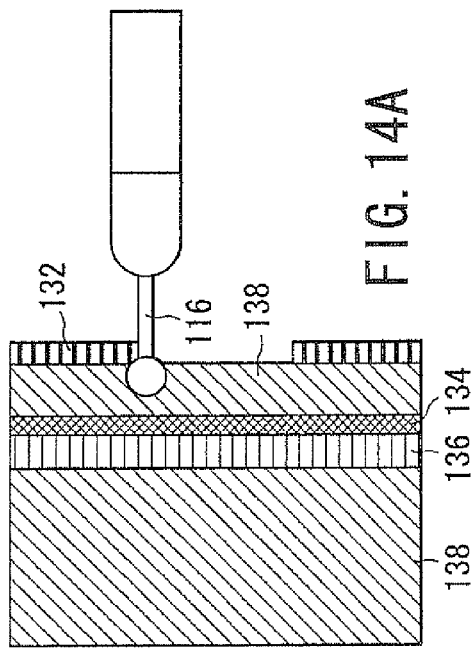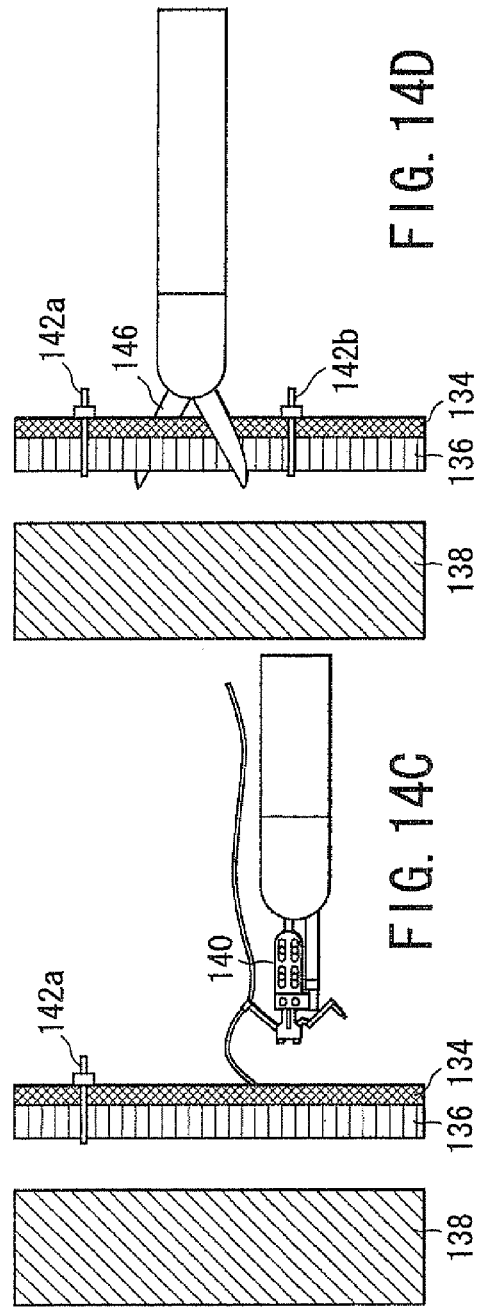

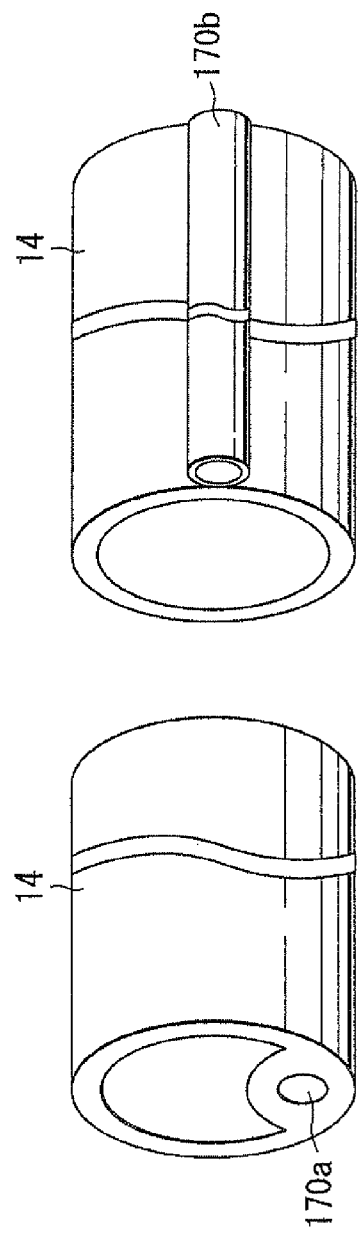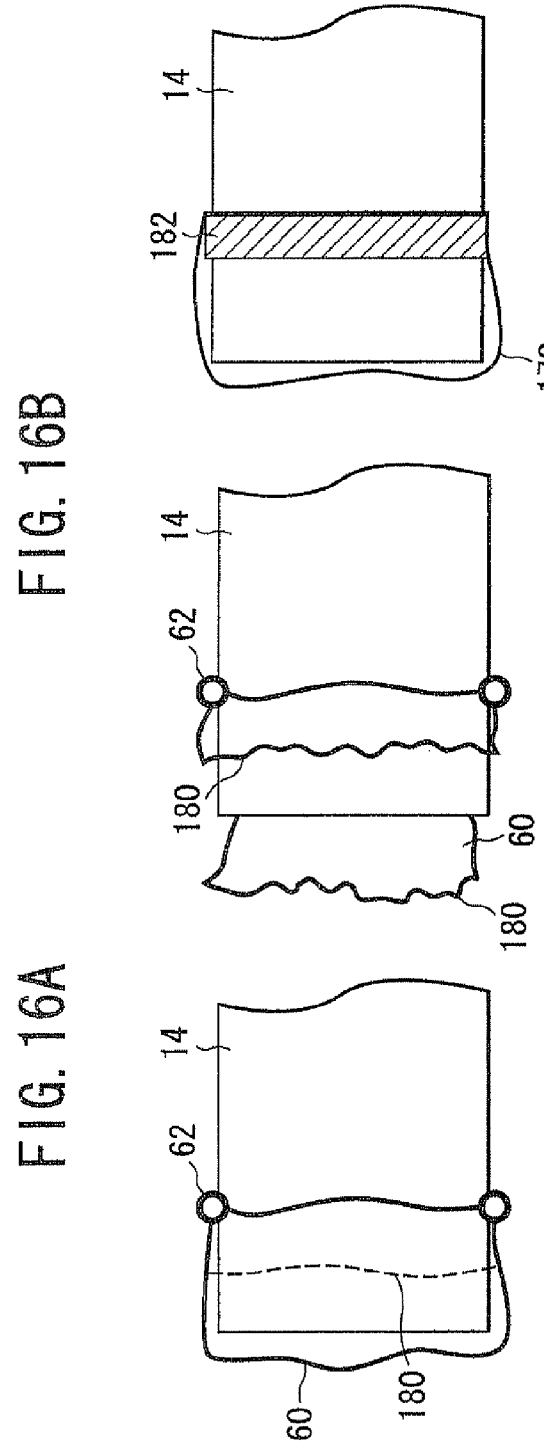

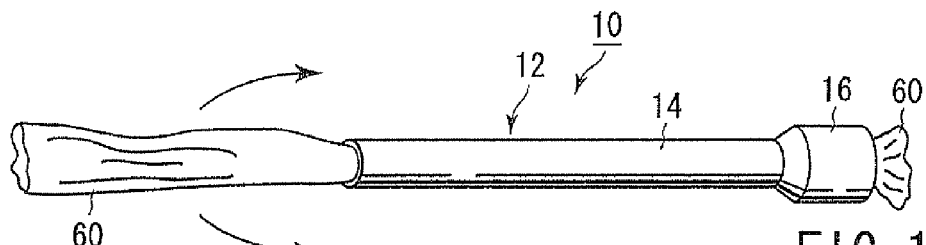
FIG. 19A
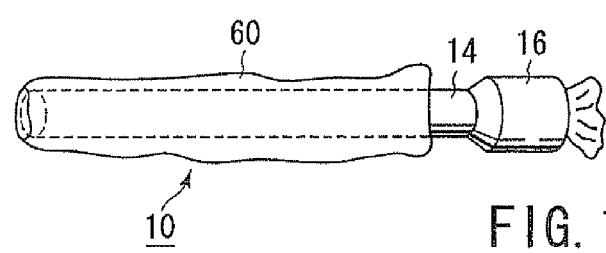
FIG. 19B
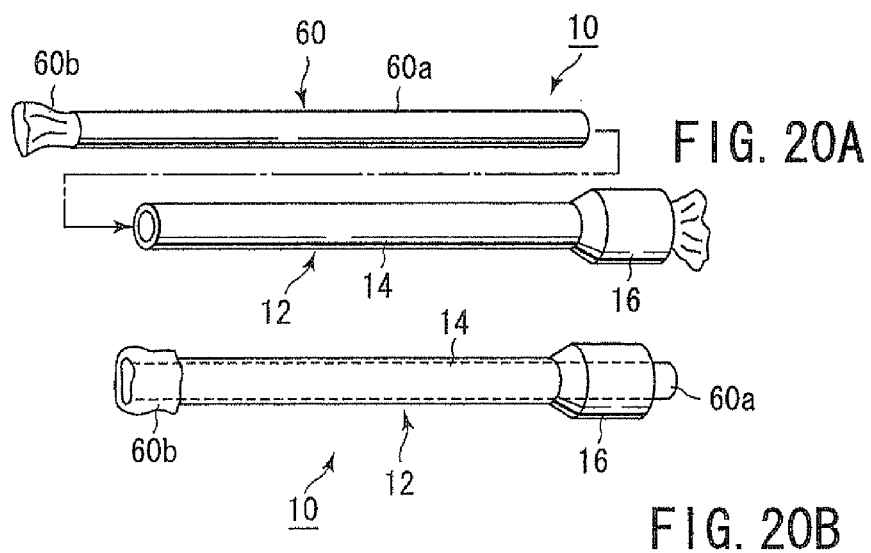
FIG. 20A
FIG. 20B
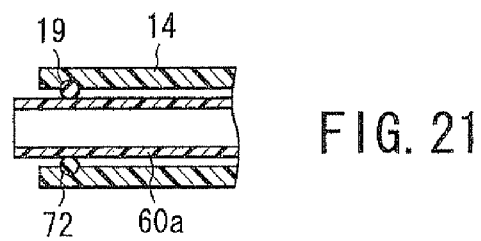
FIG. 21

OVER-TUBE, METHOD OF MANUFACTURING OVER-TUBE, METHOD OF DISPOSING OVER-TUBE, AND METHOD OF TREATMENT IN ABDOMINAL CAVITY

CROSS REFERENCE TO RELATED APPLICATION

The present application is a divisional of U.S patent application Ser. No. 10/962,000 filed on Oct. 8, 2004 now U.S. Pat. No. 7,645,230, is a Continuation Application of PCT Application No. PCT/JP2004/001363, filed Feb. 10, 2004, which was published under PCT Article 21(2) in Japanese.

This application is based upon and claims the benefit of priority from prior U.S provisional Patent Application No. 60/446,447, filed Feb. 11, 2003, the entire contents of which are incorporated herein by reference.

BACKGROUND OF THE INVENTION

1. Field of the Invention

The present invention relates to an over-tube for use, for example, in an abdominal cavity surgical operation, a method of manufacturing an over-tube, a method of disposing an over-tube, and a method of treatment in an abdominal cavity.

2. Description of the Related Art

Method of abdominal cavity surgical operations using over-tubes has been described, for example, in U.S. Pat. Nos. 5,458,181 and 5,297,536. As shown in FIG. 26, in both the methods, an over-tube 300 is inserted into an abdominal cavity from a natural opening 310 in the patient's body through a lumen wall. For example, an endoscope 320 or a treatment device 330 can be allowed to detachably access the abdominal cavity through the over-tube 300.

BRIEF SUMMARY OF THE INVENTION

One aspect of an over-tube which is used in combination with an endoscope having an elongated insertion section includes:

an over-tube main body having a distal portion on one end of an elongated tube and a proximal portion on the other end thereof and being capable of passing the insertion section of the endoscope, the over-tube main body being inserted from the distal portion thereof into a patient's body through a natural opening to access an abdominal cavity through a lumen wall from the distal portion thereof; and at least one internal cover which has a tubular shape and through which the insertion section of the endoscope is inserted in a detachably inserted state in an inner cavity of the over-tube main body, the internal cover having a distal portion which is disposed in a protruded state further on a front side from the distal portion of the over-tube main body and which covers an outer peripheral surface of the distal portion of the over-tube main body, and a proximal portion protruded on a hand side from the proximal portion of the over-tube main body, so that the internal cover is extractible from the proximal portion of the over-tube main body.

BRIEF DESCRIPTION OF THE SEVERAL VIEWS OF THE DRAWING

FIG. 2 is a sectional view showing a hand portion of the over-tube according to the first embodiment of the present invention;

FIG. 3A is a perspective view showing the vicinity of a distal end portion of a tube sheath in a state in which a coil is disposed in a wall in the over-tube according to the first embodiment of the present invention;

FIG. 3B is a sectional view showing the vicinity of the distal end portion of the tube sheath in a state in which the coil is disposed in the wall in the over-tube according to the first embodiment of the present invention;

FIG. 4A is a sectional view showing the distal end portion of the over-tube sheath showing a first step of preparing the tube sheath in a state in which the coil is disposed in the wall in the over-tube according to the first embodiment of the present invention;

FIG. 4B is a sectional view of the distal end portion of the over-tube sheath showing a second step of preparing the tube sheath in a state in which the coil is disposed in the wall in the over-tube according to the first embodiment of the present invention;

FIG. 4C is a sectional view of the distal end portion of the over-tube sheath showing a third step of preparing the tube sheath in a state in which the coil is disposed in the wall in the over-tube according to the first embodiment of the present invention;

FIG. 4D is a sectional view of the distal end portion of the over-tube sheath showing a fourth step of preparing the tube sheath in a state in which the coil is disposed in the wall in the over-tube according to the first embodiment of the present invention;

FIG. 4E is a sectional view of the distal end portion of the over-tube sheath showing a fifth step of preparing the tube sheath in a state in which the coil is disposed in the wall in the over-tube according to the first embodiment of the present invention;

FIG. 4F is a sectional view of the distal end portion of the over-tube sheath showing a sixth step of preparing the tube sheath in a state in which the coil is disposed in the wall in the over-tube according to the first embodiment of the present invention;

FIG. 4G is a sectional view of the distal end portion of the over-tube sheath after the end of the sixth step of preparing the tube sheath in a state in which the coil is disposed in the wall in the over-tube according to the first embodiment of the present invention;

FIG. 5A is a schematic sectional view showing a state in which an elastic member of a tip of an internal cover is released from an engaged state with respect to an outer peripheral portion of the over-tube sheath in the over-tube according to the first embodiment of the present invention;

FIG. 5B is a schematic sectional view showing a state in which the elastic member of the tip of the internal cover is engaged with the outer peripheral portion of the over-tube sheath in the over-tube according to the first embodiment of the present invention;

FIG. 5C is a schematic diagram showing the elastic member of the tip of the internal cover in the over-tube according to the first embodiment of the present invention;

FIG. 5D is a schematic diagram showing another elastic member of the tip of the internal cover in the over-tube according to the first embodiment of the present invention;

FIG. 5E is a schematic diagram showing a state in which another elastic member of the tip of the internal cover is modified with respect to FIG. 5D in the over-tube according to the first embodiment of the present invention;

FIG. 7 is a schematic perspective view showing a state in which the endoscope is inserted in the over-tube according to the first embodiment of the present invention;

FIG. 8 is a schematic perspective view showing that the internal cover is extracted from the over-tube main body in a state in which the distal end of the over-tube is inserted in a lumen wall according to the first embodiment of the present invention;

FIG. 14A is a schematic diagram showing a state in which a serous membrane of a stomach is excised with the incision instrument by the vagus nerve separation;

FIG. 14B is a schematic diagram showing a state in which blood vessel, nerve, and fat are peeled with the peeling instrument by the vagus nerve separation;

FIG. 14C is a schematic diagram showing a state in which the blood vessel and nerve are ligated with a ligation instrument by the vagus nerve separation;

FIG. 14D is a schematic diagram showing a state in which the blood vessel and nerve between the ligated parts are separated with a separation instrument by the vagus nerve separation;

FIG. 16A is a schematic perspective view showing a state in which the inside of the tube sheath of the over-tube is formed into double lumen according to the first embodiment of the present invention;

FIG. 16B is a schematic perspective view showing a state in which a tubular member is attached to the outside of the tube sheath of the over-tube according to the first embodiment of the present invention;

FIG. 17A is a schematic side view showing that the internal cover having perforations formed in a tip thereof is engaged with the outer peripheral surface of the tube sheath in the over-tube according to the first embodiment of the present invention;

FIG. 17B is a schematic side view showing that the tip of the internal cover whose perforations in the tip are cut is engaged with the outer peripheral surface of the tube sheath in the over-tube according to the first embodiment of the present invention;

FIG. 18 is a schematic side view showing a state in which the tip of the internal cover is engaged with the outer peripheral surface of the tube sheath by an adhesive tape on the distal end in the over-tube according to the first embodiment of the present invention;

FIG. 19A is an exploded perspective view of the over-tube according to a second embodiment of the present invention;

FIG. 19B is a perspective view showing an outline of the over-tube according to the second embodiment of the present invention;

FIG. 20A is an exploded perspective view of the over-tube according to a third embodiment of the present invention;

FIG. 20B is a perspective view showing an outline of the over-tube according to the third embodiment of the present invention;

FIG. 21 is a schematic sectional view of a distal end portion of the over-tube according to a fourth embodiment of the present invention;

DETAILED DESCRIPTION OF THE INVENTION

Best modes (hereinafter referred to as the embodiments) for carrying out the present invention will be described hereinafter with reference to the drawings.

First, an over-tube 10 according to a first embodiment will be described with reference to FIGS. 1A to 15C.

Figure 1A:
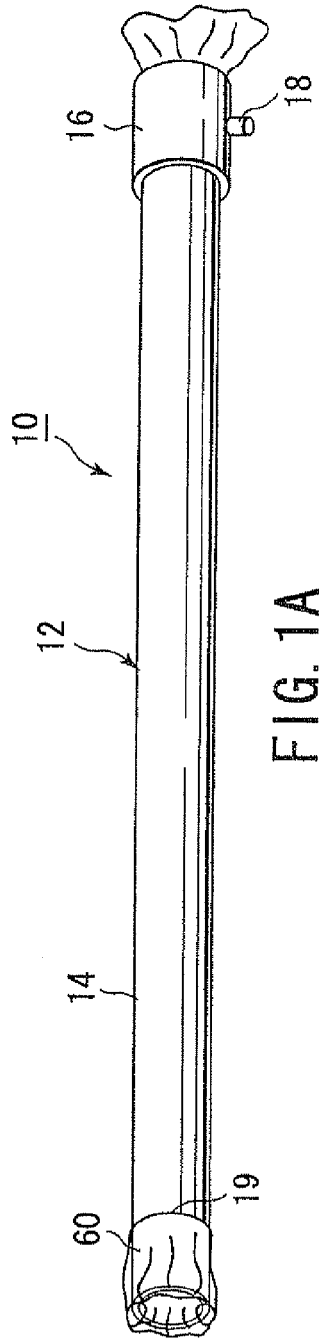
FIG. 1A is a perspective view showing an appearance of an over-tube according to a first embodiment of the present invention.
Figure 1B:
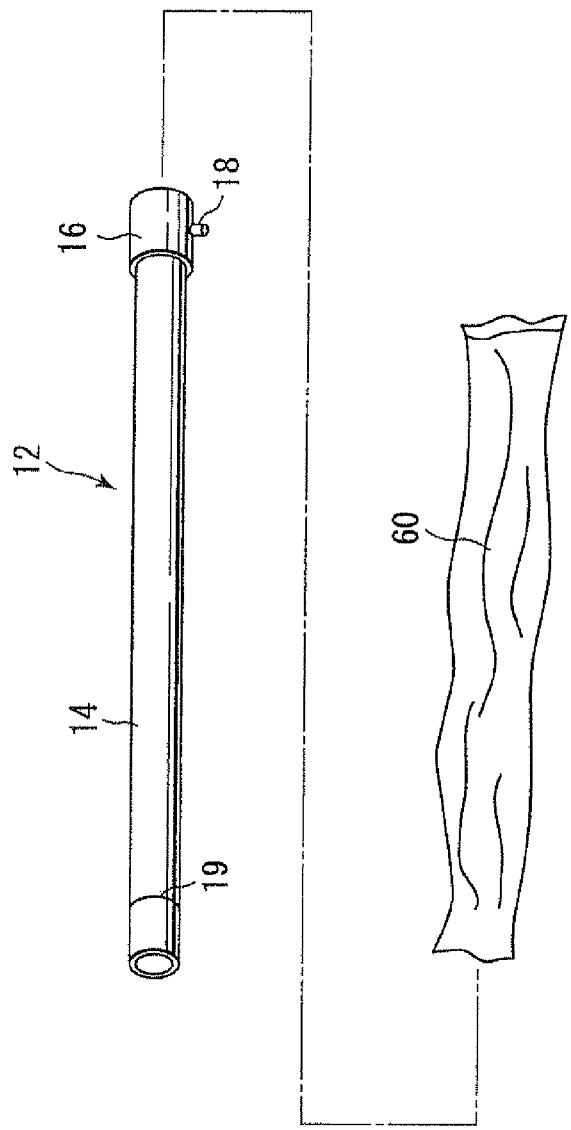
FIG. 1B is an exploded perspective view of the over-tube according to the first embodiment of the present invention.

The over-tube 10 shown in FIGS. 1A and 1B is used for allowing, for example, an endoscope or the like to access an abdominal cavity from a natural opening (mouth or anus) in the patient's body through a lumen wall.

As shown in FIG. 1A, the over-tube 10 includes an elongated over-tube main body 12. The main body 12 includes an elongated over-tube sheath 14, and an over-tube hand portion 16 disposed on a proximal end portion of the sheath 14.

The over-tube sheath 14 includes one lumen (passage) for passing at least an endoscope 90 described later. A section of the sheath 14 has, for example, a schematically circular shape (round type). A distal end portion and proximal end portion of the sheath 14 communicate with each other through an inner cavity.

In a material of the tube sheath 14, an elastic material is used including polymer resins having stretching properties, such as vinyl chloride, vinyl chloride-vinyl acetate copolymer, polyurethane, and fluorine plastic, natural or synthetic rubber latex, synthetic rubbers such as silicon rubber, isoprene rubber, and neoprene rubber, or elastomers containing polystyrene, polyester, polyether, and polyolefin as main components.

A length of the over-tube sheath 14 is set to such an extent that the sheath 14 is inserted via the natural opening in the human body and is capable of reaching a target part in the body. The length of the sheath 14 is, for example, 300 mm to 5000 mm, especially preferably 500 mm to 1000 mm.

The outer diameter of the sheath 14 is set to such an extent that the sheath 14 can be inserted from the natural opening in the human body. The outer diameter of the sheath 14 is, for example, 5 mm to 32 mm, especially preferably 5 mm to 27 mm.

The inner diameter of the sheath 14 is set to such an extent that an insertion section of the endoscope 90 or a treatment device can be inserted. The inner diameter of the sheath 14 is, for example, 3 mm to 30 mm, especially preferably 3 mm to 25 mm.

An annular groove (detachable portion) 19 is formed in the outer peripheral surface in the vicinity of the distal end portion of the sheath 14 in a peripheral direction. A tip of an internal cover 60 described later is engaged with and fixed to the annular groove 19. It is to be noted that convex portions may be formed at predetermined distance intervals on the outer peripheral surface in such a manner as to engage with an elastic member 62 described later, instead of the annular groove 19. When the elastic member 62 is formed of a material that does not easily slip with respect to the outer peripheral surface of the sheath 14, the annular groove 19 does not have to be disposed, and the outer peripheral surface may be formed to be flat.

A suction port 18 formed of a tubular member is protruded on the outer peripheral surface of the over-tube hand portion 16. By the suction port 18, the inner cavity of the sheath 14 communicates with an outer portion of the hand portion 16. With respect to the suction port 18, for example, a suction tube (not shown) connected to a suction machine (not shown) is connected, or a cap (not shown) is attached in order to maintain air tightness in the over-tube main body 12.

As shown in FIG. 2, the hand portion 16 includes a hard pipe-shaped member 20 formed, for example, of a resin material. On a distal end side of the pipe-shaped member 20, a cylindrical first small-diameter portion 20a formed into a diameter smaller than that of the proximal portion is disposed concentrically and integrally with the pipe-shaped member 20. Further inside the first small-diameter portion 20a, a cylindrical second small-diameter portion 20b is concentrically disposed. The proximal end portion of the sheath 14 is pressed in and held between the first small-diameter portion 20a and the second small-diameter portion 20b. In this manner, the over-tube sheath 14 is connected to the tube hand portion 16. The proximal end portion of the sheath 14 and the hand portion 16 (pipe-shaped member 20) are held between the first and second small-diameter portions 20a, 20b, and fixed in an auxiliary manner, for example, by ultrasonic fusion bonding, thermal fusion bonding, bonding by solvent adhesive, screwing and the like.

On the outer peripheral surface from the first small-diameter portion 20a to the vicinity of the proximal end portion of the sheath 14, a cylindrical cover member 20c which covers the first small-diameter portion 20a and the proximal end portion of the sheath 14 on an outer peripheral side is disposed. The cover member 20c has a function of preventing the sheath 14 from being broken, while a connected state of the sheath 14 to the hand portion 16 is strengthened.

In the inner portion (inner cavity) of the pipe-shaped member 20, a valve mechanism (isolation mechanism) is disposed on a proximal end side from a position in which the suction port 18 is protruded on order to prevent sucked or fed air from being released to the outside from the inner portion of the over-tube main body 12. The valve mechanism includes cylindrical or annular first to third valve guards 22, 24, 26 arranged parallel to each other along an axial direction of the main body 12. Outer peripheral portions of valves 28, 28 are held between the first and second valve guards 22, 24 and between the second and third valve guards 24, 26. That is, the outer peripheral portions of the valves 28, 28 are held by holding portions 30, 30 formed between facing end portions of the first and second valve guards 22, 24 and between facing end portions of the second and third valve guards 24, 26.

The outer peripheral surfaces of the first to third valve guards 22, 24, 26 are preferably formed in such a manner as to adhere to an inner wall of the pipe-shaped member 20. On the other hand, a minimum inner-diameter portion of an inner peripheral surface of each of the valve guards 22, 24, 26 has a diameter smaller than that of each of the holding portions 30, 30 which hold the respective valves 28, 28. Therefore, these holding portions 30, 30 of the valves 28, 28 comprise relief portions 32, 32 gently tilted (dimension change) toward the above-described minimum inner-diameter portion. These relief portions 32, 32 are constituted to secure deformation regions where the valves 28, 28 deform. The diameter of the minimum inner-diameter portion is preferably set to have a dimension which is equal to the inner diameter of the over-tube sheath 14 or which is larger by ten percent.

The valves 28, 28 are formed of elastic members such as rubber materials, have flexibility, and are formed, for example, into disc shapes, and through-holes are formed in middle portions of the valves 28, 28. The diameter of each through-hole of the valves 28, 28 is smaller than an outer diameter of the insertion section of the endoscope 90. Therefore, for example, when the endoscope 90 is inserted into the pipe-shaped member 20, the valves 28, 28 adhere to the outer peripheral surface of the insertion section of the endoscope 90, and airtightness between interior and exterior of the body is maintained.

The over-tube main body 12 is formed in this manner.

Next, a structure of the over-tube sheath 14 will be described. As shown in FIGS. 3A and 3B, a reinforcing coil 40 is concentrically disposed between the inner wall and outer wall (in the wall) of the sheath 14. The sheath 14 obtains desired softness and strength by this reinforcing coil 40. This reinforcing coil 40 is formed, for example, of a SUS material, and has a desired spring property. An element wire diameter of the reinforcing coil 40 is preferably set, for example, to about 0.5 mm. In a case where a thickness of the sheath 14 is about 1 mm, when the element wire diameter is less than 0.4 mm, resistance to buckling of the sheath 14 is poor. When the element wire diameter exceeds 0.5 mm, the flexibility of the sheath 14 is uniformly poor.

As shown in FIG. 3A, a tip of the reinforcing coil 40 is bent back into a state in which any peak portion does not exist, and bonded to a bond portion 42 in an appropriate position of a part of the reinforcing coil 40 itself by welding. Therefore, the distal end portion of the coil 40 is prevented from being exposed to the inside/outside of the tube sheath 14 while the tip itself of the reinforcing coil 40 breaks through the inner wall or outer wall of the tube sheath 14.

As shown in FIG. 3B, a portion shown by code L in which the reinforcing coil 40 does not exist is disposed, for example, by about 20 mm to 80 mm in the tip of the over-tube sheath 14. The distal end portion of the sheath 14 is more flexible than a portion provided with the coil 40. Therefore, an insertion property with respect to the internal of the body can be enhanced as compared with a case where the portion provided with the coil 40 is disposed on the distal end portion of the sheath 14.

A method of manufacturing the sheath 14 in which this reinforcing coil 40 is buried between the inner wall and the outer wall of the over-tube sheath 14, that is, in the wall will be described with reference to FIGS. 4A to 4G.

As shown in FIG. 4A, the reinforcing coils 40, and a tube 44 formed of a thermoplastic resin and having an inner diameter smaller than an outer diameter of the reinforcing coil 40 are prepared (first step). For example, polyurethane or the like is used in the tube 44 formed of the thermoplastic resin.

As shown in FIG. 4B, the diameter of the reinforcing coil 40 is reduced, and the coil 40 is inserted into the lumen of the tube 44. A cored bar 46 is inserted inside the lumen of the tube 44, and inside the reinforcing coil 40 (second step). The cored bar 46 is set at an outer-diameter dimension equal to the inner-diameter dimension at a time when the cored bar 46 is formed as the over-tube sheath 14. The cored bar 46 may have a tubular shape having a lumen inside. The cored bar 46 may have an inner lumen, and a micro-hole extending through the cored bar 46 on the side of the outer peripheral surface from the lumen.

As shown in FIG. 4C, the tube 44 in a state of the second step is coated with a heat-shrinkable tube 48 (third step). The heat-shrinkable tube 48 has a length substantially equal to that of the tube 44, or a length a little larger than that of the tube 44, and is thermally shrunk inwards in a diametric direction at a temperature exceeding a melting point of the tube 44.

In a state in which the third step ends, a heating step (fourth step) is performed. The heat-shrinkable tube 48 is heated to a temperature at which the tube is shrunk inwards in the diametric direction. In this case, when the cored bar 46 is tubular and has micro-holes, a step of decompressing a tubular inner portion of the cored bar 46 may be added.

In the fourth step, the tube 44 is heated at a temperature higher than the melting point of the tube 44. Therefore, the tube 44 itself is molten. The heat-shrinkable tube 48 disposed on the outer peripheral side of the tube 44 is shrunk inwards in the diametric direction. The tube 44 is pressed inwards following the shrinking of the heat-shrinkable tube 48, and both the inner diameter and the outer diameter of the tube 44 are shrunk. At the time of the melting of the tube 44, a force to urge the reinforcing coil 40 in such a manner as to reduce the diameter is not transmitted to the reinforcing coil 40. Therefore, the reinforcing coil 40 swells outwards in the diametric direction, and is buried in the wall of the molten tube 44. On the other hand, the diameter of the heat-shrinkable tube 48 is reduced, and the outer diameter of the cored bar 46 is held in an unchanged state. Therefore, the reinforcing coil 40 is held inwards in the diametric direction in a reduced-diameter state against an urging force by the heat-shrinkable tube 48. Therefore, the heat-shrinkable tube 48 and tube 44 are cooled. Then, as shown in FIG. 4D, the heat-shrinkable tube 48 and the tube 44 are integrated to form the over-tube sheath 14 in a state in which the reinforcing coils 40 are buried in the tube 44. It is to be noted that when the cored bar 46 provided with the micro-holes in the fourth step is used, and the inside of the sheath 14 is decompressed, a movement in which the sheath 14 is reduced (formed) is promoted. Therefore, the sheath 14 can be prepared in a short time.

Thereafter, as shown in FIG. 4E, the cored bar 46 is extracted from the sheath 14 (fifth step).

Subsequently, a sixth step is performed. As shown in FIG. 4F, a die 50 is used in which concave portions 52 having R shapes (semispherical sectional shapes) are formed into annular shapes. The distal end portion of the sheath 14 is heated and attached onto the concave portions 52 of the die 50. As shown in FIG. 4G, the tip of the sheath 14 is formed into a rounded state.

By the above-described first to sixth steps, unlike an extrusion step or a dipping step, the sheath 14 containing the reinforcing coils 40 can be easily manufactured without preparing an exclusive-use manufacturing apparatus.

Since a large pressure is not loaded onto the sheath 14 as in the extrusion step, the reinforcing coils 40 are prevented from being irregularly shifted in the wall of the sheath 14, and the sheath 14 whose quality has been stabilized can be manufactured. Since a resin does not have to be dissolved in a solvent as in the dipping step, it is not necessary to study solubility of the resin with respect to the solvent, and the sheath can be easily manufactured.

As shown in FIGS. 1A and 1B, the internal cover (cylindrical member) 60 is detachably attached from the proximal end portion of the tube main body 12 to the distal end portion thereof in the inner cavity of the over-tube main body 12 formed in this manner. The internal cover 60 is formed of polymer resin materials such as vinyl chloride, polyethylene, and polypropylene, and formed into a soft film which is not easily broken and which has permeability to a gas such as an ethylene oxide gas and/or resistance to γ-rays. The internal cover 60 preferably has antibacterial specifications.

As shown in FIG. 5A, an annular elastic member 62 is disposed on the distal end portion (distal end portion) of the internal cover 60. The vicinity of the distal end portion of the internal cover 60 protrudes outwards from the distal end portion of the over-tube sheath 14. As shown in FIGS. 1A and 5B, a portion (distal end portion) protruding with respect to the distal end portion of the over-tube sheath 14 is folded back outwards. As shown in FIG. 5B, the elastic member 62 is engaged with the annular groove 19 in the outer peripheral surface of the over-tube sheath 14.

In this case, as shown in FIG. 1A, the proximal end portion (proximal portion) of the internal cover 60 protrudes further on a hand side from the proximal end portion of the hand portion 16 of the tube main body 12. When the internal cover 60 is pulled on a hand side, the engagement of the elastic member 62 in the annular groove 19 is released in the outer peripheral surface in the vicinity of the distal end portion of the tube sheath 14. Therefore, the internal cover 60 is recovered with respect to the over-tube main body 12.

It is to be noted that as the annular elastic member 62, as shown in FIG. 5C, a ring having a shrinking property, for example, a rubber material is used. A C-shaped elastic member 66 may be used such as a metal or a resin which is elastically deformable, for example, between a shrunk state shown in FIG. 5D and an expanded state shown in FIG. 5E and which has a spring property.

The over-tube 10 is formed in this manner.

Next, a function of the over-tube 10 having this constitution will be described with reference to FIGS. 6 to 15C.

First, the internal cover 60 shown in FIG. 1B is inserted into the inner cavity of the over-tube main body 12. The tip of the internal cover 60 is folded back outwards at the tip of the over-tube sheath 14. The elastic member 62 on the tip of the internal cover 60 is engaged with the annular groove 19 in the outer peripheral surface of the sheath 14. Therefore, as shown in FIG. 1A, the over-tube 10 is prepared. In this case, the proximal end of the internal cover 60 is protruded from the over-tube hand portion 16 on the hand side.

Figure 6:
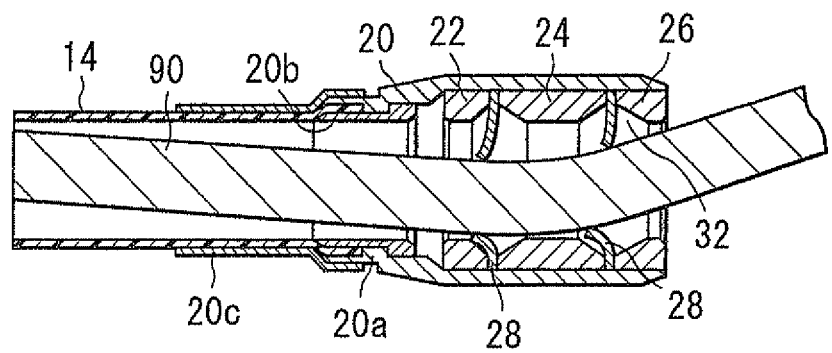
FIG. 6 is a schematic sectional view of a hand portion in a state in which an endoscope is inserted in an over-tube main body in the over-tube according to the first embodiment of the present invention.

The endoscope 90 and a treatment device (not shown) are passed through the over-tube 10 from a proximal end portion side toward a distal end portion side. That is, as shown in FIG. 6, the endoscope 90 and the treatment device are inserted through the inner cavity of the internal cover 60. When the endoscope 90 or the treatment device is inserted into the over-tube main body 12 in this manner, the endoscope 90 or the treatment device is deflected inside the hand portion 16. The minimum inner-diameter portions of the first to third valve guards 22, 24, 26 are formed into dimensions each of which is substantially equal to the inner diameter of the sheath 14, and therefore the endoscope 90 is urged by the valves 28, 28 in such a manner that the endoscope is centered on the side of the middle of the hand portion 16. When the endoscope 90 or the treatment device is inserted, the valves 28, 28 are gently deflected along tilts of the relief portions 32, 32. In this case, the hand side of the hand portion 16 and the distal end portion side of the hand portion 16 are brought into mutually airtight states by the valves 28, 28.

As shown in FIG. 7, the over-tube 10 provided with the endoscope 90 in this manner is inserted into a lumen wall 100 from the natural opening in the patient's body. The lumen wall 100 is opened using the endoscope 90 and the treatment device.

After the distal end portion of the sheath 14 of the over-tube main body 12 is engaged with and fixed to the opening in the lumen wall 100, the endoscope 90 and the treatment device are pulled and extracted with respect to the proximal end portion of the main body 12 on the hand side. In this state, the internal cover 60 in the main body 12 is pulled with respect to the proximal end portion of the main body 12 on the hand side.

As shown in FIG. 5A, an engaged state of the elastic member 62 of the tip of the internal cover 60 with the annular groove 19 in the vicinity of the distal end portion of the main body 12 (sheath 14) is released. The elastic member 62 of the tip of the internal cover 60 is drawn into the inner cavity of the main body 12 between the lumen wall 100 and the vicinity of distal end portion of the main body 12 (sheath 14). That is, by the urging force at a time when the engaged state of the elastic member 62 of the internal cover 60 with the annular groove 19 in the outer peripheral surface of the main body 12 is released, the main body 12 and the lumen wall 100 are elastically deformed, and the elastic member passes between the both. Therefore, while the elastic member 62 of the internal cover 60 returns to a straight state from the folded-back state, the distal end portion of the main body 12 is drawn into the inner cavity.

As shown in FIG. 8, the internal cover 60 is extracted through the inner cavity of the main body 12. For example, deposits such as mucus/contents in the patient's lumen are attached to the inner peripheral surface of the extracted internal cover 60. Therefore, when the internal cover 60 is extracted from the main body 12, the deposits are removed. The outer wall of the internal cover 60 is brought into contact only with the inner wall of the sheath 14. Therefore, the inner cavity of the over-tube main body 12 is held in a substantially sterile state.

Figure 9:
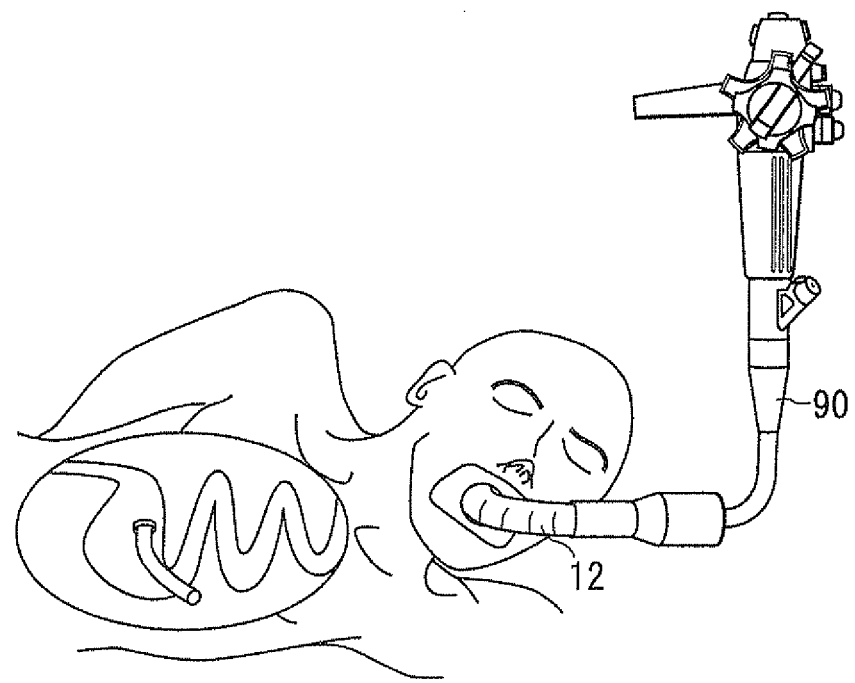
FIG. 9 is a schematic diagram showing that the over-tube and endoscope are introduced into a target body part in a state in which the endoscope is introduced in the over-tube main body in the over-tube according to the first embodiment of the present invention.

After extracting the internal cover 60 in this manner, the sterilized new endoscope 90 and treatment device are inserted into the abdominal cavity via the inner cavity of the over-tube main body 12 to perform an endoscopic treatment as shown in FIG. 9.

The endoscopic treatment in the abdominal cavity via the over-tube 10 will be described hereinafter with reference to FIGS. 10A to 15C.

First, esophagus cardiac musculi incision will be described.

As described above, the over-tube 10 having the endoscope 90 and a treatment device for an opening, which have been inserted in the inner cavity of the tube 10, is inserted into the stomach from patient's mouth through the esophagus. The stomach is opened on a stomach body front wall side with the treatment device for the opening. The over-tube 10 is engaged with and fixed to the opening (not shown). Thereafter, the endoscope 90 and the treatment device for the opening are extracted from the inner cavity of the over-tube main body 12. Subsequently, the internal cover 60 is extracted. A sterilized new endoscope 90, different from the extracted endoscope, is inserted into the abdominal cavity through the inner cavity of the over-tube main body 12.

The tip of the endoscope 90 is guided into a lower esophagus 110 in the abdominal cavity. As a method of guiding the endoscope 90, the following system is used. For example, a method of inserting a light emitting instrument into an organ in the abdominal cavity to guide the endoscope by light, a method of two-dimensionally guiding the endoscope by a fluoroscope, a method of three-dimensionally guiding the endoscope by an endoscope insertion shape observation apparatus; and the like are used.

Figure 10B:
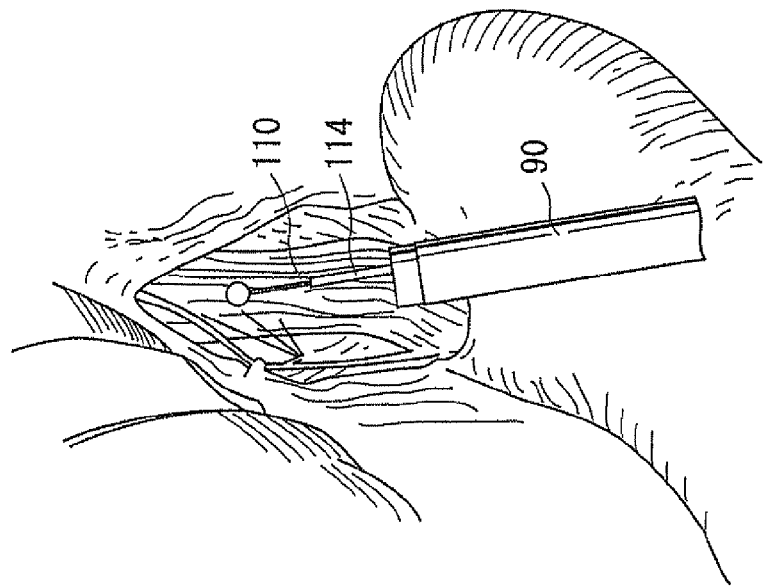
FIG. 10B is an outline view showing a state in which the esophagus cardiac musculi of the lower esophagus is marked with a marking instrument by the esophagus cardiac musculi incision.
Figure 10A:
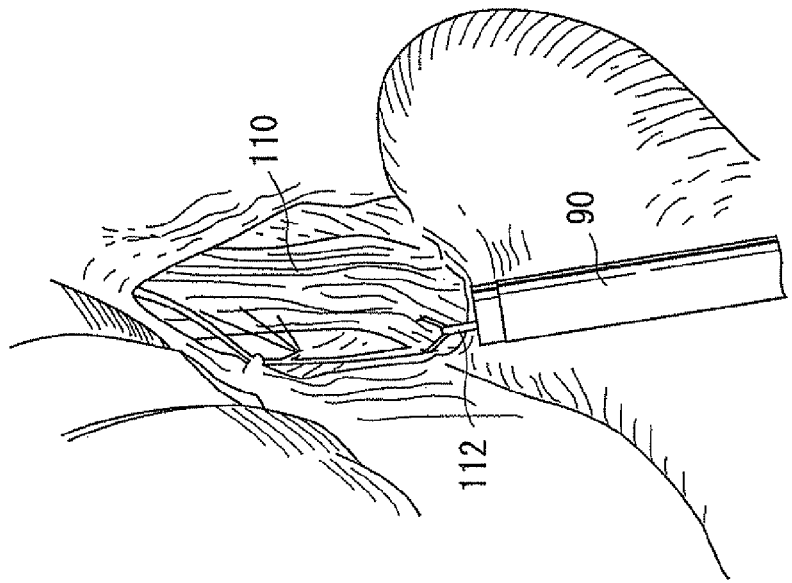
FIG. 10A is an outline view showing a state in which a lower esophagus is peeled with a peeling instrument by esophagus cardiac musculi incision.

As shown in FIG. 10A, the lower esophagus 110 is peeled and exposed by a peeling instrument 112 passed through a channel (not shown) of the endoscope 90. As the peeling instrument 112, multiple degrees of freedom forceps, rod-shaped peeling forceps, needle-shaped/hook-shaped/spatula-shaped/clamp forceps type/peeling forceps type/scissors forceps type/IT knife/snare type high-frequency incision instruments, needle-shaped/hook-shaped/spatula-shaped/clamp forceps type ultrasonic solidifying incision instruments, laser treatment devices and the like are used.

As shown in FIG. 10B, an incised part of a esophagus cardiac musculi of the lower esophagus 110 is marked by a marking instrument 114. As the marking instrument 114, a tattooing by local-injection needle, clip, electric heating instruments such as a high-frequency incision instrument and a heat knife and the like are used.

Figure 11B:
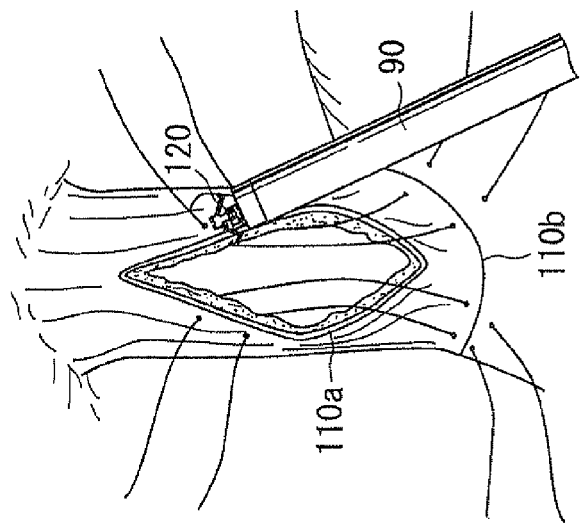
FIG. 11B is an outline view showing a state in which the part incised by the esophagus cardiac musculi incision is stitched with a stitching instrument.
Figure 11C:
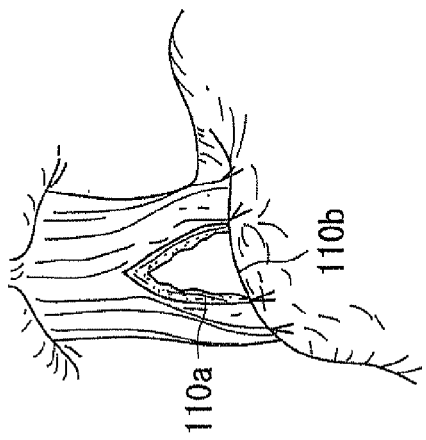
FIG. 11C is an outline view showing a stitched state with the stitching instrument by the esophagus cardiac musculi incision.
Figure 11A:
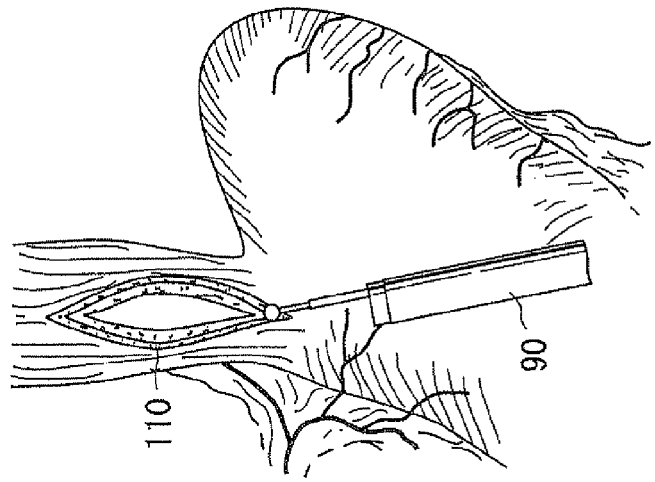
FIG. 11A is an outline view showing a state in which a marked part is incised with an incision instrument by the esophagus cardiac musculi incision.

As shown in FIG. 11A, a cardiac musculi layer of a marked part is incised by an incision instrument 116. As the incision instrument 116, scissors forceps/bow-shaped/needle-shaped/hook-shaped/spatula-shaped/clamp forceps type/peeling forceps type/scissors forceps type/IT knife high-frequency incision instruments, needle-shaped/hook-shaped/spatula-shaped/clamp forceps type ultrasonic solidifying incision instrument, laser treatment device, a high-frequency incision cap, Malecott knife and the like are used. It is to be noted that the incision instrument 116 is preferably provided with a guide mechanism for protecting nerve/blood vessel/tissue and the like.

As shown in FIG. 11B, knotting stitching is performed to knot-bond an esophagus side musculi incised edge 110a and a stomach serous membrane 110b outside a stomach side incised edge, incised with the incision instrument 116, by a stitching instrument 120 (see FIG. 11C). As the stitching instrument 120, a thread stitching unit, clip, stapler, T-bar stitching unit and the like are used.

Figure 12:
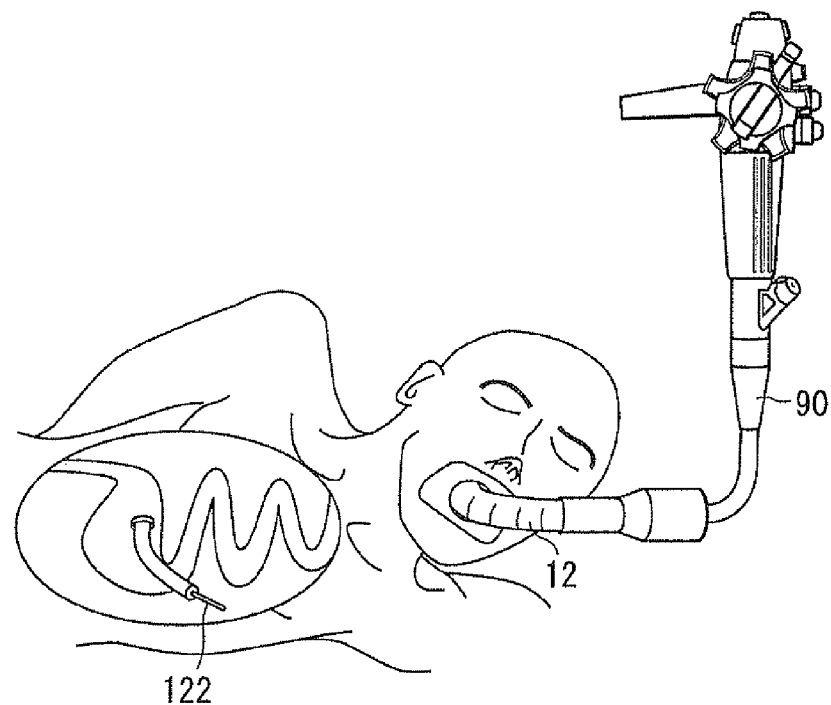
FIG. 12 is an outline view showing that the abdominal cavity is cleaned with a cleaning water supply/suction instrument via the endoscope in a state in which the over-tube and endoscope are introduced into the target part of the body according to the first embodiment of the present invention.

After ending this treatment, as shown in FIG. 12, the interior of the abdominal cavity is cleaned with a warm physiological salt solution by a cleaning water supply/suction instrument 122. The cleaning water may be supplied from a cleaning tube (not shown), or supplied from the endoscope 90 or the inner cavity of the over-tube main body 12. The cleaning water may be sucked by a suction tube (not shown), or sucked by the endoscope 90 or the inner cavity of the main body 12.

After extracting the endoscope 90 from the inner cavity of the over-tube main body 12, the over-tube 10 is extracted. Subsequently, the stomach opening is closed.

Next, vagus nerve separation will be described.

In the same manner as in the esophagus cardiac musculi incision, the over-tube 10 is fixed to the opening, and the sterilized endoscope 90 is inserted into the abdominal cavity through the inner cavity of the over-tube main body 12.

Figure 13:
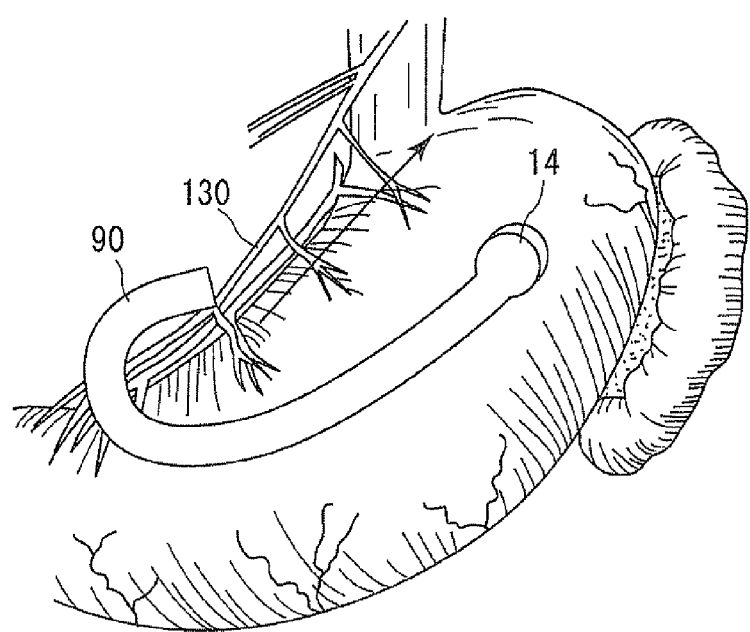
FIG. 13 is an outline view showing a state in which a vagus nerve branch is accessed by vagus nerve separation.

As shown in FIG. 13, the tip of the endoscope 90 is guided into a vagus nerve branch 130 on the side of a mouth of an antropyloric branch in the above-described guiding method. Moreover, as shown in FIG. 14A, a stomach serous membrane 132 is excised by the above-described incision instrument 116 passed through a channel (not shown) of the endoscope 90.

As shown in FIG. 14B, a blood vessel 134 and a nerve 136 are peeled off from a fat 138 by the above-described peeling instrument 112.

As shown in FIG. 14C, opposite sides of separated parts of the blood vessel 134 and nerve 136 are ligated by a ligation instrument 140 to form ligated portions 142a, 142b. As the ligation instrument 140, a thread stitching unit, clip, snare and the like are used.

As shown in FIG. 14D, the blood vessel 134 and nerve 136 between the ligated portions 142a, 142b are separated by a separation instrument 146. As the separation instrument 146, scissors forceps, bow-shaped/needle-shaped/hook-shaped/spatula-shaped/clamp forceps type/peeling forceps type/scissors forceps type/snare type high-frequency incision instruments, needle-shaped/hook-shaped/spatula-shaped/clamp forceps type ultrasonic solidifying incision instrument, laser treatment device and the like are used.

At this time, in the case of bleeding, blood clots/stops by a hemostatic instrument (not shown). As the hemostatic instrument, a clip, snare, thread stitching unit, high-frequency clamp forceps, heat probe, ultrasonic solidifying incision device, high-frequency solidifier, argon plasma solidifying device, laser treatment device and the like are used.

Thereafter, the endoscope 90 is guided to a stomach body upper surface rear part. A rear stem of a vagus nerve is exposed using the peeling instrument 112. In this case, other nerves/blood vessels are protected beforehand using a blood vessel/nerve protection instrument. As the protection instrument, a protective tube, pressure discharge by balloon, traction by thread and the like are used. The rear stem of the blood vessel/vagus nerve is ligated, and thereafter separated.

As shown in FIG. 12, the interior of the abdominal cavity is cleaned with the warm physiological salt solution by the cleaning water supply/suction instrument 122. Moreover, after extracting the endoscope 90 from the inner cavity of the over-tube main body 12, the over-tube 10 is extracted. Subsequently, the stomach wall opening is closed.

Next, appendix excision will be described.

In the same manner as in the esophagus cardiac musculi incision, the over-tube 10 is fixed to the opening, and the sterilized endoscope 90 is inserted into the abdominal cavity through the inner cavity of the over-tube main body 12.

Figures 15A, 15B:
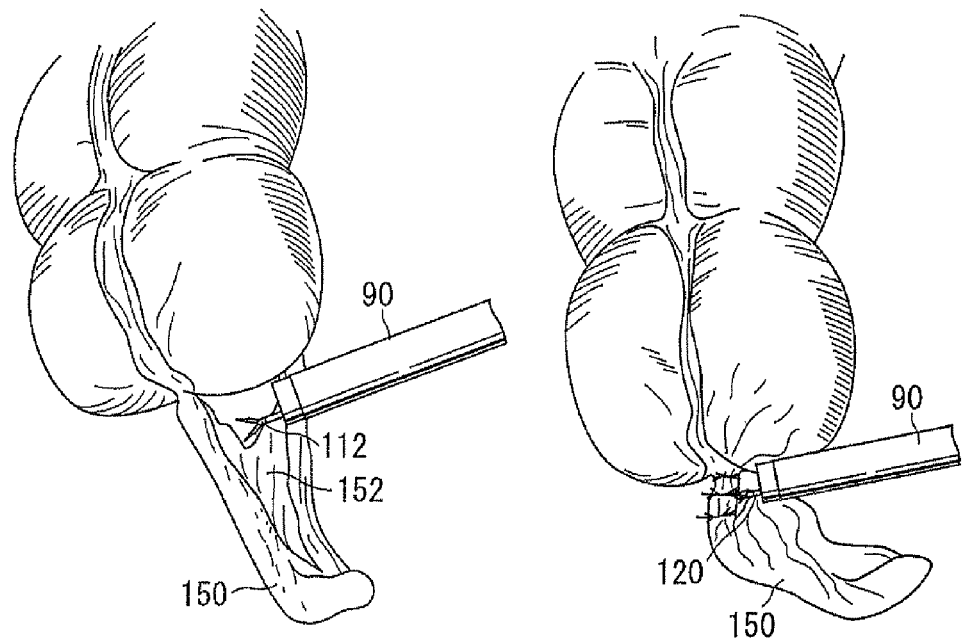
FIG. 15A is an outline view showing a state in which mesoappendix is allowed to dehisce with the peeling instrument by appendix excision.
FIG. 15B is an outline view showing a state in which opposite sides of the separated part of appendicular root are ligated with the ligation instrument by the appendix excision.

The tip of the endoscope 90 is guided into an appendix part in the above-described guiding method. Moreover, as shown in FIG. 15A, a mesoappendix 152 of an appendix 150 is divided by the above-described peeling instrument 112 passed through the channel (not shown) of the endoscope 90. An appendix artery/vein is separated by the above-described separation instrument 146.

As shown in FIG. 15B, opposite sides of a separated part of a root of the appendix 150 are ligated by the above-described ligation instrument (stitching instrument) 120.

Figure 15C:
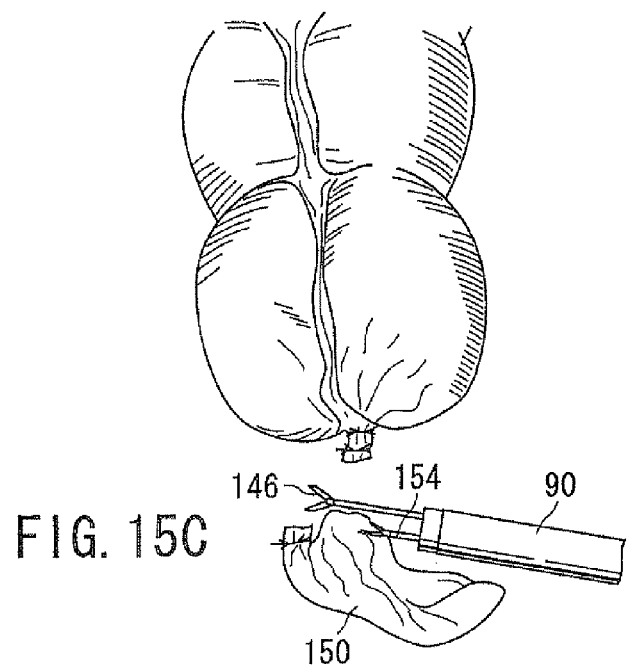
FIG. 15C is an outline view showing a state in which the appendicular root is separated with the separation instrument by the appendix excision.

As shown in FIG. 15C, the root of the appendix 150 is separated by the above-described separation instrument 146. At this time, the cut appendix 150 is clamped and recovered by a clamping instrument 154. As the clamping instrument 154, clamp forceps, suction cap and the like are used.

The cut appendix 150 is recovered to the exterior of the body by a recovery instrument (not shown). As the recovery instrument, clamp forceps, multi-leg type clamp forceps, basket, suction and the like are used.

As shown in FIG. 12, the interior of the abdominal cavity is cleaned with the warm physiological salt solution by the cleaning water supply/suction instrument 122. After extracting the endoscope 90 from the inner cavity of the over-tube main body 12, the over-tube 10 is extracted. Subsequently, the stomach wall opening is closed.

Besides the above-described operations, other operations, local injection or chemical scattering with respect to the tissue in the abdominal cavity, biopsy or cytodiagnosis, image diagnosis of a local part by an ultrasonic searcher and the like can be performed.

As described above, according to the embodiment, the following effects are obtained.

In the over-tube hand portion 16, by functions of the minimum inner-diameter portions of the first to third valve guards 22, 24, 26 and the valves 28, 28, the endoscope 90 inserted in the inner cavity is centered. Inner holes (through-holes) of the valves 28, 28 are brought into close contact with the outer periphery of the endoscope 90, and high airtightness can be secured. Since the relief portions 32, 32 are formed in the first to third valve guards 22, 24, 26, the valves 28, 28 are freely deformed even at the time of the insertion of the endoscope 90, and a resistance to a large load is maintained. Accordingly, a large load can be prevented from being applied. Then, in the valve mechanism, an insertion property of the endoscope 90 can be kept high, and durability of the valve mechanism itself can be secured.

FIG. 16A shows a first modification of the over-tube main body 12. In the modification, the over-tube sheath 14 is provided with a channel (tube sheath, lumen) 170a into which a treatment device can be inserted separately from the inner cavity into which, for example, the endoscope 90 is inserted. The channel 170a is attached to (formed in) the inside of the over-tube sheath 14. For example, the channel 170a may be formed integrally with the over-tube sheath 14.

The channel 170a is formed, for example, of a polymer resin material, and is formed as a tube sheath having a round section. The channel 170a has at least one lumen (passage) for passing the treatment device.

A length of the channel 170a is set to such an extent that the tube sheath 170a can be inserted into the body together with the over-tube sheath 14. The length is, for example, 300 mm to 5000 mm, especially preferably 500 mm to 1000 mm. The inner diameter of the channel 170a is set to such an extent that the clamp forceps pass. The diameter is, for example, 1 mm to 20 mm, especially preferably 2 mm to 10 mm.

FIG. 16B shows a second modification of the over-tube main body 12. In this modification, the over-tube sheath 14 is provided with an external tube (channel, lumen) 170b into which the treatment device can be inserted, for example, in the same axial direction separately from the inner cavity in which, for example, the endoscope 90 is inserted. The external tube 170b is attached to the outer side of the over-tube sheath 14 in an external state. The external tube 170b may be fixed to the over-tube sheath 14 by pressing-in, bonding (e.g., ultrasonic fusion bonding, thermal fusion bonding, solvent adhesive) and the like. It is to be noted that the length and the inner diameter of the external tube 170b are equal to those of the channel 170a of the first modification of the over-tube main body 12.

FIGS. 17A and 17B show a first modification of the internal cover 60. In this modification, as shown in FIG. 17A, a structure which can be easily cut, such as a perforation (cut portion) 180, is disposed in the peripheral direction in the vicinity of the tip of the internal cover 60. It is to be noted that the tip of the internal cover 60 is engaged with the annular groove 19, for example, by the elastic member 62. When the internal cover 60 is pulled from the hand side of the over-tube main body 12, as shown in FIG. 17B, the internal cover 60 on the hand side from the perforation 180 is cut via the perforation 180 and recovered.

FIG. 18 shows a second modification of the internal cover 60. In the modification, the tip of the internal cover 60 includes, for example, an adhesive tape (detachable portion) 182 which is a detachable portion (adhesive means) on the outer peripheral surface (annular groove 19) in the vicinity of the distal end portion of the over-tube sheath 14. When the internal cover 60 is pulled on the hand side, the adhesive tape 182 peels from the outer peripheral portion of the over-tube sheath 14, and the internal cover 60 is recovered. In this case, the annular groove 19 does not have to be formed by a degree of adhesion of the detachable portion.

Next, a second embodiment will be described with reference to FIGS. 19A and 19B. Since the embodiment is a modification of the first embodiment, the same members as those described in the first embodiment are denoted with the same reference numerals, and detailed description thereof is omitted. This also applies to the following third to eighth embodiments.

As shown in FIG. 19A, in an over-tube 10 according to this embodiment, a length of an internal cover 60 is formed into a length about twice that of an over-tube sheath 14.

In this case, substantially the whole periphery of the outer peripheral surface of the sheath 14 can be covered in a state in which the proximal end portion of the internal cover 60 is protruded on the hand side of the hand portion 16.

It is to be noted that the elastic member 62 (see FIG. 5B) on the tip of the internal cover 60 or the annular groove 19 in the outer peripheral surface of the sheath 14 may be omitted.

The over-tube 10 in this state has a function similar to that described above in the first embodiment.

Next, a third embodiment will be described with reference to FIGS. 20A and 20B.

An over-tube 10 according to the embodiment is different in a structure of an internal cover 60.

As shown in FIG. 20A, the internal cover 60 integrally includes a tube member (shield tube) 60a inserted through an over-tube main body 12, and a tubular film-like member 60b protruded from the tip of the tube member 60a.

The internal cover 60 is inserted toward a base end from a tip of the over-tube main body 12. As shown in FIG. 20B, the film-like member 60b is folded back to cover the outer periphery of the tip of an over-tube sheath 14.

The over-tube 10 in this state has a function similar to that described above in the first embodiment.

Next, a fourth embodiment will be described with reference to FIG. 21.

As shown in FIG. 21, an annular groove 19a is formed in an inner peripheral surface of a tip of an over-tube sheath 14. A tube member (cylindrical member) 60a is disposed in an over-tube main body 12. Since an O-ring (sealing member) 72 is disposed in the annular groove 19a, the outer peripheral surface of the tube member 60 is held into an airtight state on the hand side from the O-ring 72.

The over-tube 10 in this state has a function similar to that described above in the first embodiment.

Next, a fifth embodiment will be described with reference to FIGS. 22A and 22B.

Figure 22A:
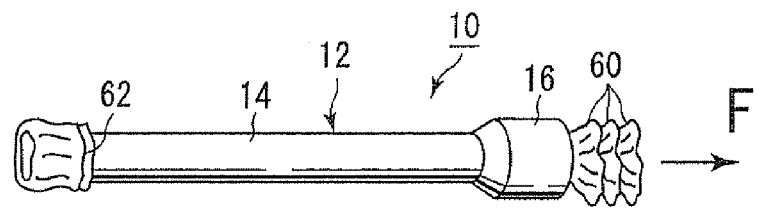
FIG. 22A is a perspective view showing an outline of the over-tube according to a fifth embodiment of the present invention.
Figure 22B:
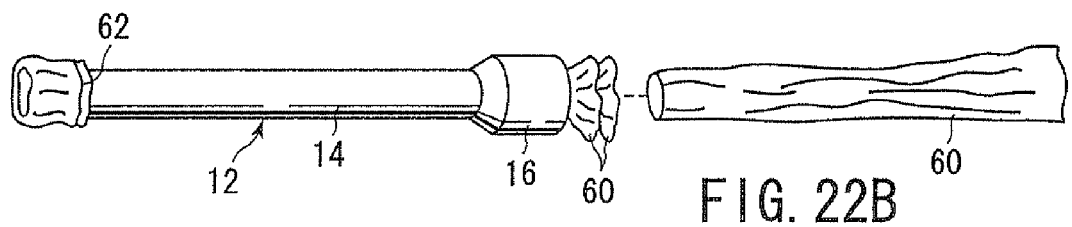
FIG. 22B is an exploded perspective view of the over-tube according to the fifth embodiment of the present invention.

As shown in FIGS. 22A and 22B, a plurality of internal covers 60 are disposed inside an over-tube main body 12.

An over-tube 10 in this state has a function similar to that described above in the first embodiment.

According to the over-tube 10 of this embodiment, even when an endoscope 90 or a treatment device is replaced many times, the internal covers 60 are removed one by one, treatment can be performed in a state in which a sterile state is constantly maintained.

It is to be noted that the internal cover 60 is not limited to a film configuration, and a tubular configuration may be used.

Next, a sixth embodiment will be described with reference to FIGS. 23A to 23D.

Figure 23A:
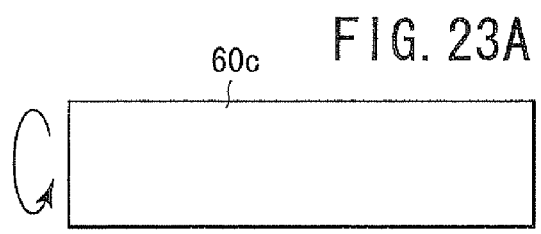
FIG. 23A is a schematic diagram showing a sheet member in the over-tube according to a sixth embodiment of the present invention.

As shown in FIG. 23A, in an internal cover 60, a sheet-like member 60c is used instead of a film-like member.

Figure 23B:
FIG. 23B is a schematic diagram showing a rounded state of the sheet member in the over-tube according to the sixth embodiment of the present invention.

As shown in FIG. 23B, this sheet-like member 60c is rounded, inserted into an over-tube main body 12, and used.

Figure 23C:
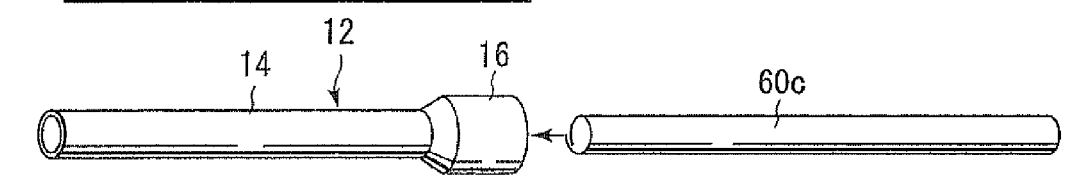
FIG. 23C is an exploded perspective view of the over-tube according to the sixth embodiment of the present invention.

As shown in FIG. 23C, the sheet-like member 60c in a rounded state is inserted toward a distal end portion from a proximal end portion of the over-tube main body 12.

Figure 23D:
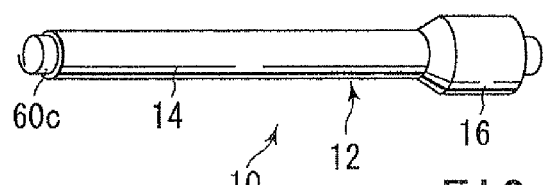
FIG. 23D is a perspective view showing an outline of the over-tube according to the sixth embodiment of the present invention.

An over-tube 10 formed as shown in FIG. 23D for use has a function similar to that described above in the first embodiment.

Next, a seventh embodiment will be described with reference to FIG. 24.

Figure 24:
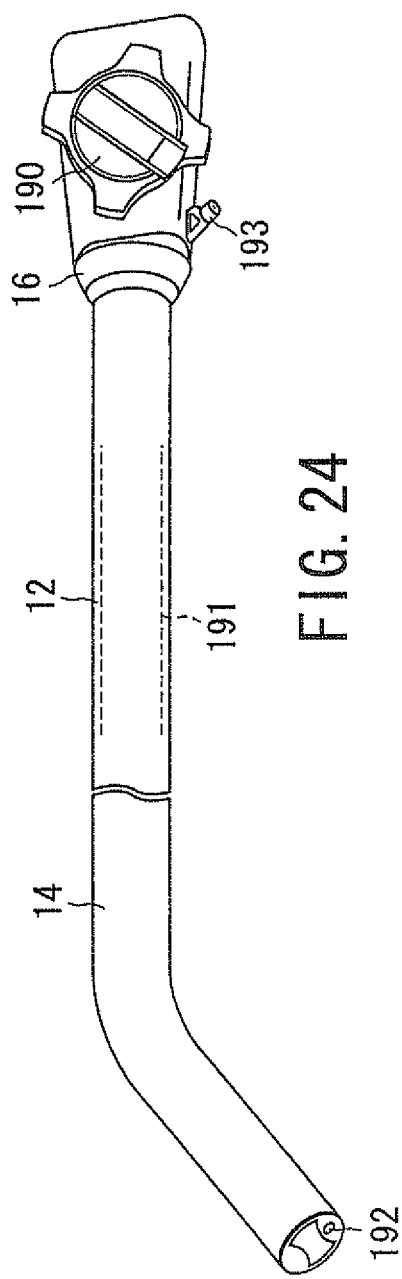
FIG. 24 is a perspective view showing an over-tube provided with a bending mechanism according to a seventh embodiment of the present invention.

As shown in FIG. 24, an over-tube main body 12 of an over-tube 10 according to the embodiment includes a bending mechanism. An over-tube hand portion 16 of the main body 12 is provided with a knob 190 for bending (bending operation portion) together with a valve mechanism (not shown). In the main body 12, for example, one to four wires 191 are disposed. The distal end portion of each wire 191 is connected to the distal end portion of an over-tube sheath 14. The proximal end portion of the wire 191 is extended on a hand portion 16 side. The knob 190 for bending is connected to a sprocket for driving, which tightens or loosens the wire 191.

It is to be noted that the over-tube main body 12 further includes a channel. An opening 192 of the channel is formed in the distal end portion of the over-tube sheath 14. The hand portion 16 includes a forceps plug 193 of the channel.

Next, a function of the over-tube 10 having this constitution will be described.

An internal cover 60 is disposed in an inner cavity of the over-tube 10. An endoscope 90 and a treatment device are inserted into the inner cavity of the internal cover 60 beforehand. When the over-tube 10 in this state is inserted to a lumen wall 100 (see FIGS. 7 and 8) through a natural opening in the patient's body, a predetermined part is accessed using the bending mechanism of the over-tube 10.

The over-tube 10 in a state in which the endoscope 90 and the treatment device are inserted into the inner cavity is inserted from the natural opening in the human body, and the knob 190 for bending is operated. By the operation of the knob 190 for bending, the sprocket for driving is driven to tighten or loosen the wire 191, and the over-tube sheath 14 is bent in a desired direction.

The over-tube main body 12 is bent in this manner to thereby bend the endoscope 90 and treatment device following the main body 12, while the distal end portion of the over-tube sheath 14 is introduced into a desired position (lumen wall 100 shown in FIGS. 7 and 8).

By the use of a channel in the over-tube main body 12, for example, air feeding/water feeding, suction and the like are performed.

Since other functions are similar to those of the first embodiment, description thereof is omitted.

As described above, according to this embodiment, the following effect is obtained. It is to be noted that description of the effect described in the first embodiment is omitted.

Since the bending mechanism for bending the over-tube 10 is disposed, the over-tube 10 is easily allowed to access a target part in the lumen wall 100.

Even in a state in which an endoscope and the like are not disposed inside the over-tube 10, the air feeding/water feeding, suction and the like can be performed.

Next, an eighth embodiment will be described with reference to FIG. 25.

Figure 25:
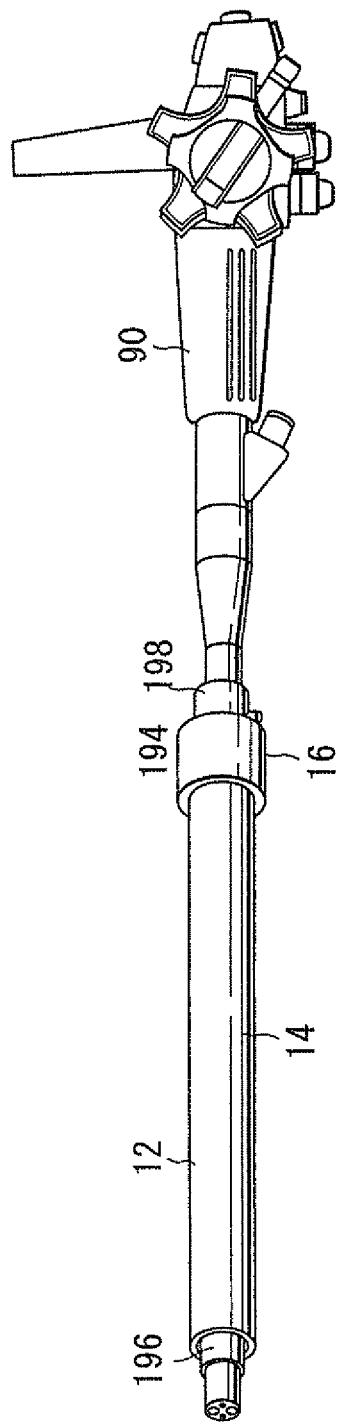
FIG. 25 is a schematic perspective view showing a state in which the endoscope and an introducer are inserted into an inner cavity of the over-tube according to an eighth embodiment of the present invention.
Figure 26:
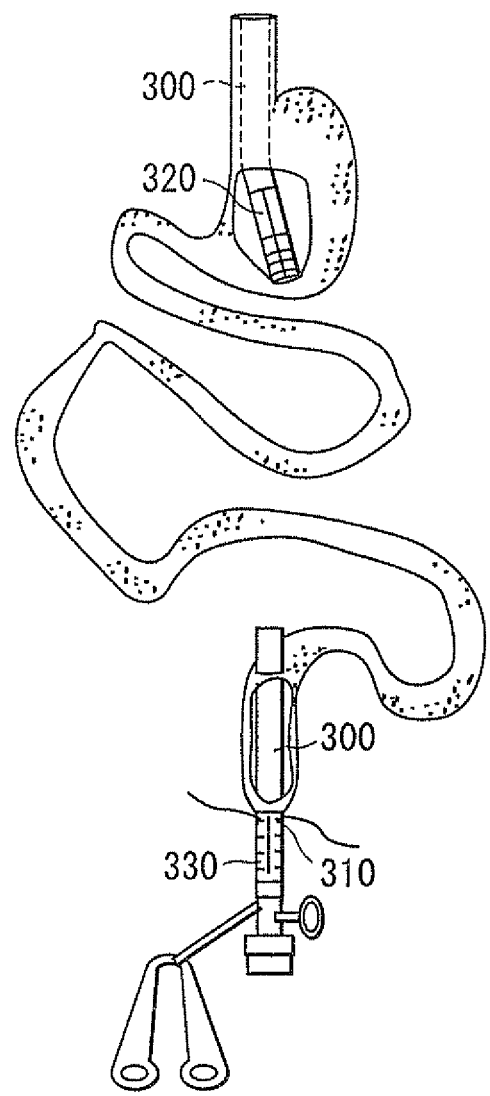
FIG. 26 is a schematic diagram showing an prior art.

As shown in FIG. 25, an introducer 194 is inserted into an over-tube main body 12. An endoscope 90 and a treatment device are inserted in an inner cavity of this introducer 194.

The introducer 194 includes a tubular introducer sheath 196, and an introducer hand portion 198 disposed on a base end of the introducer sheath 196. The introducer sheath 196 is formed, for example, of a polymer resin material, and a section is formed as a round tube. The introducer sheath 196 includes one lumen (passage) for passing at least the endoscope 90.

A length of the introducer sheath 196 is set to such an extent that the sheath 196 can be inserted from the natural opening in the human body to reach the target part in the body. The length is, for example, 300 mm to 5000 mm, especially preferably about 500 mm to 1000 mm. The outer diameter of the introducer sheath 196 is set to such an extent that the sheath 196 can be inserted from the natural opening in the human body. The diameter is, for example, 5 mm to 30 mm, especially preferably about 5 mm to 27 mm. The inner diameter of the introducer sheath 196 is set to such an extent that the endoscope 90 can be inserted into the sheath 196. The diameter is, for example, 3 mm to 30 mm, especially preferably 3 mm to 25 mm.

The introducer hand portion 198 is a hard pipe-like member formed, for example, of a resin material, and is pressed in the introducer sheath 196, and bonded, for example, by ultrasonic fusion bonding, thermal fusion bonding, and solvent adhesive, or fixed by screwing. To prevent air sucked or fed in the tube main body 12 (introducer 194) from being released, the same valve mechanism (not shown) as that described in the first embodiment is disposed in the introducer hand portion 198, and airtightness between interior and exterior of the body is maintained.

Next, a function of an over-tube 10 having this constitution will be described.

The internal cover 60 is disposed in the inner cavity of the over-tube 10. The endoscope 90 and the treatment device are inserted in the inner cavity of the internal cover 60 beforehand. The over-tube 10 in this state is inserted into the lumen wall 100 (see FIGS. 7 and 8) through the natural opening in the patient's body. The target lumen wall 100 is opened by the endoscope 90 and the treatment device. After opening the wall, the over-tube main body 12 is fixed to the opening (lumen wall 100). The endoscope 90 and the treatment device are extracted. The internal cover 60 in the over-tube main body 12 is extracted from the hand side of the over-tube 10.

The sterilized introducer 194 is inserted into the over-tube main body 12 instead of the internal cover 60. The endoscope 90 and the treatment device are inserted into the inner cavity of the introducer 194 to access the target part in the abdominal cavity, and an endoscopic treatment is performed.

Since other functions are similar to those described in the first embodiment, description thereof is omitted.

As described above, according to this embodiment, the following effect is obtained. It is to be noted that the description of the effect described in the first embodiment is omitted.

The introducer 194 is disposed in the inner cavity of the over-tube 10 whose distal end portion is engaged with the lumen wall 100 (opening). Therefore, the endoscope 90 and the treatment device can be more securely protruded from the distal end portion of the over-tube 10 engaged with the lumen wall 100. Then, accessibility in the abdominal cavity can be enhanced.

Since the introducer 194 has the valve mechanism, an airtight/liquid-tight state can be maintained, and permeation of bacteria by insertion/detachment of the endoscope 90 or the treatment device can be prevented.

Several embodiments have been concretely described with reference to the drawings, but the present invention is not limited to the above-described embodiment, and all implementations performed without departing from the scope are included.

What is claimed is:

1. A method of disposing an over-tube including an inner cavity and an internal cover disposed in the inner cavity thereof, each of the inner cavity and the internal cover being able to alternatively insert an endoscope and a treatment device, the method, comprising:
    inserting the endoscope into the internal cover;
    inserting the over-tube into a body cavity from a natural opening in a patient's body in a state that the endoscope is inserted into the internal cover;
    arranging a distal end portion of the over-tube within a lumen wall of the body cavity;
    removing the endoscope and the internal cover from the inner cavity of the over-tube to a proximal side of the over-tube; and
    inserting the treatment device into the inner cavity of the over-tube,
    wherein:
    a tip end of the internal cover is engaged with an outer peripheral portion of the distal end portion of the over-tube, and
    the removing the internal cover from the inner cavity of the over-tube includes pulling off the internal cover to the proximal side of the over-tube after the over-tube is arranged within the lumen wall of the body cavity, releasing an engagement between the tip end of the internal cover and the outer peripheral portion of the over-tube, and extracting the internal cover from the inner cavity of the over-tube.

2. The method of the treatment in the abdominal cavity according to claim 1, comprising:
    introducing a treatment device further through the inner cavity of the over-tube;
    guiding the treatment device into a position to be treated;

treating the position to be treated with the treatment device;

extracting the treatment device from the inner cavity of the over-tube; and extracting the over-tube.

3. The method of the treatment in the abdominal cavity according to claim 2, further comprising cleaning the inside of the abdominal cavity.

4. The method of the treatment in the abdominal cavity according to claim 3, wherein the cleaning of the inside of the abdominal cavity comprises sucking a cleaning solution disposed in the abdominal cavity.

5. The method of disposing the over-tube according to claim 1, wherein the tip end of the internal cover protruding with respect to the distal end portion of the over-tube is folded back outwards, and engaged with the distal end portion of the over-tube.

6. The method of disposing the over-tube according to claim 1, wherein the internal cover is disposed in the inner cavity of the over-tube so as to cover an entire inner wall of the over-tube from a proximal end to the distal end portion of the over-tube.

7. The method of disposing the over-tube according to claim 1, wherein the arranging of the distal end portion of the over-tube includes a state that a proximal end of the internal cover is protruded from a proximal end of the over-tube to the proximal side of the over-tube.

* * * * *